United States Patent [19]

Wuest et al.

[11] Patent Number: 5,298,755
[45] Date of Patent: Mar. 29, 1994

[54] OPTICAL IONIZATION DETECTOR

[75] Inventors: Craig R. Wuest, Danville; Mark E. Lowry, Castro Valley, both of Calif.

[73] Assignee: The United States of America as represented by the United States Department of Energy, Washington, D.C.

[21] Appl. No.: 11,635

[22] Filed: Feb. 1, 1993

[51] Int. Cl.$^5$ ............................................. G01T 1/185
[52] U.S. Cl. .................................... 250/389; 250/374; 250/375
[58] Field of Search .............. 250/389, 374, 375, 382, 250/385.1, 390.01

[56] References Cited

U.S. PATENT DOCUMENTS

| | | | |
|---|---|---|---|
| 4,320,299 | 3/1982 | Bateman et al. | 250/374 |
| 4,426,580 | 1/1984 | Smith | 250/374 |
| 4,522,495 | 6/1985 | Shajenko | 356/345 |
| 4,733,967 | 3/1988 | Sommargren | 356/361 |
| 4,829,821 | 5/1989 | Carome | 73/516 |
| 4,950,074 | 8/1990 | Fabricius et al. | 356/133 |
| 5,004,914 | 4/1991 | Vali et al. | 250/227.27 |

Primary Examiner—Paul M. Dzierzynski
Assistant Examiner—Richard Hanig
Attorney, Agent, or Firm—Henry Sartorio; Roger S. Gaither; William R. Moser

[57] ABSTRACT

An optical ionization detector wherein a beam of light is split so that one arm passes through a fiber optics and the other arm passes through a gas-filled region, and uses interferometry to detect density changes in a gas when charged particles pass through it. The gas-filled region of the detector is subjected to a high electric field and as a charged particle traverses this gas region electrons are freed from the cathode and accelerated so as to generate an electron avalanche which is collected on the anode. The gas density is effected by the electron avalanche formation and if the index or refraction is proportional to the gas density the index will change accordingly. The detector uses this index change by modulating the one arm of the split light beam passing through the gas, with respect to the other arm that is passed through the fiber optic. Upon recombining of the beams, interference fringe changes as a function of the index change indicates the passage of charged particles through the gaseous medium.

20 Claims, 1 Drawing Sheet

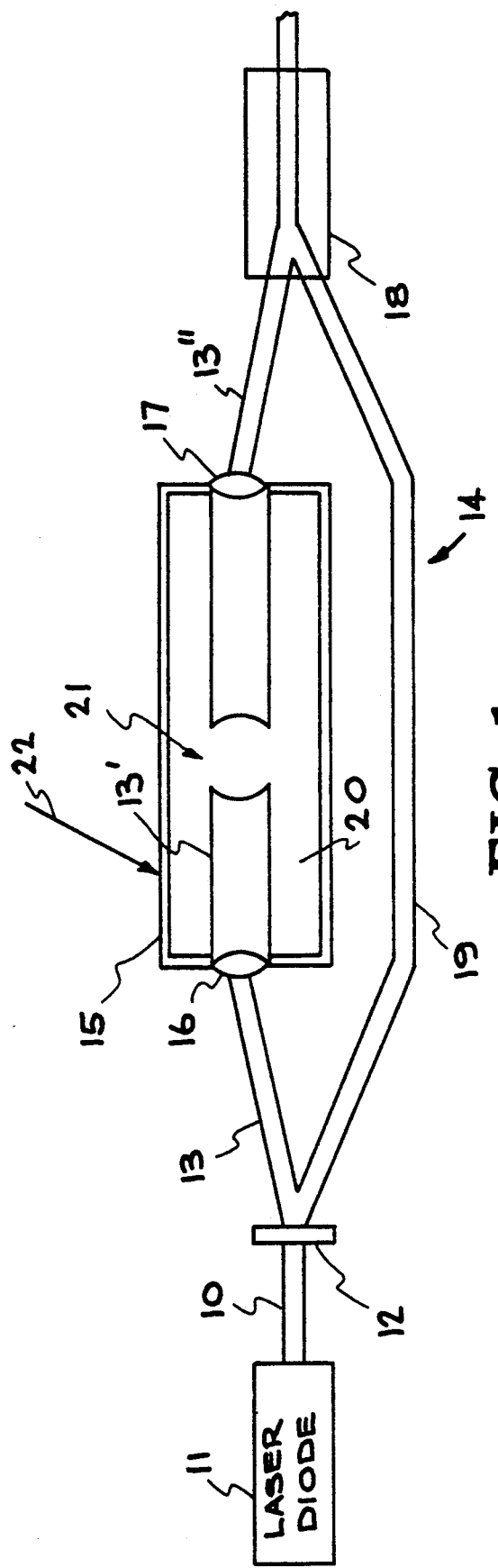
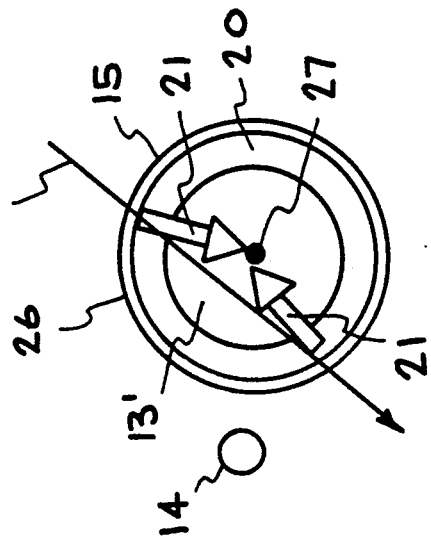
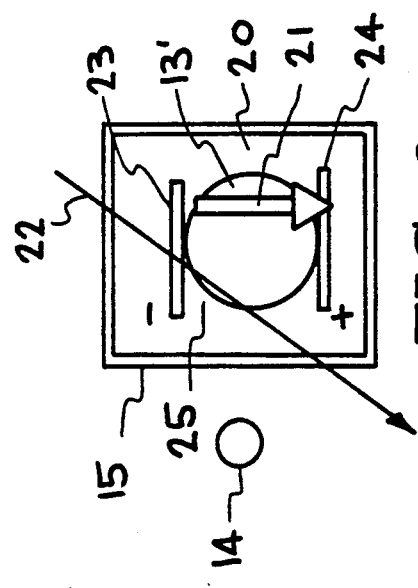
FIG. 1
FIG. 2
FIG. 3

OPTICAL IONIZATION DETECTOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

This invention relates to the detection of ionizing radiation, particularly to a means for directing ionizations from natural and man-made sources, and more particularly to a detector of ionizing radiation which uses optical interferometry to detect density changes in a gas when charged particles pass through it.

Various types of detectors and detector systems have been developed for the detection of various levels of electromagnetic radiation and are utilized for various applications including surface contamination due to radiation, testing odd-shaped metal components used in processing radioactive materials, for sensing the position of neutral particles, measuring physical phenomena using optical interferometry, changes in the refractive index of a substance, optical fiber accelerometers, and for detecting chemical vapors in the air, to name as few applications. These prior known detectors and systems are exemplified by U.S. Pat. No. 5,004,914 issued Apr. 2, 1991 to V. Vali et al.; U.S. Pat. No. 4,950,074 issued Aug. 21, 1990 to N. Fabricius et al.; U.S. Pat. No. 4,829,821 issued May 16, 1989 to E. F. Carome; U.S. Pat. No. 4,733,967 issued Mar. 29, 1988 to G. E. Sommargron; and U.S. Pat. No. 4,522,495 issued Jun. 11, 1985 to P. Shajenko. In each of the above-referenced patents, a beam of electromagnetic radiation is first split, at least one arm of the beam is processed, and then the two beam arms are combined for determining the relation of characteristics of the arm of energy processed compared to the characteristics of the arm not processed.

While these prior detection devices and system are effective for certain applications, there is a need, particularly within the high energy physics community, to detect ionizing radiation, such as electrons, gamma rays, and muons, within extremely large sampling volumes of proposed detector systems to be built at the next generation of high energy particle accelerators. As an example, at the Superconducting Super Collider, two large detector systems are being proposed which will contain many different types of ionization counters to detect the by-products of high energy proton-proton collisions. These detector systems will use an extremely large number of separate detectors to reconstruct the many possible particle tracks, providing measurements of position, energy and momentum. This extremely large number of separate detectors makes it advantageous to consider replacing standard electronics with electro-optic components. Electro-optics allows for high density routing of fiber-optic cables, optical triggering, and immunity to stray radiation and electrical noise. Thus, with the proposed use of electro-optics, there is a need for an optical ionization detector for detecting charged particles.

The present invention fills this need by providing such an optical detector of ionizing radiation and which uses optical interferometry to detect density changes in a gas when charged particles pass through the gas.

SUMMARY OF THE INVENTION

An object of the present invention is to provide a detector of ionizing radiation to detect density changes in a gas and change the index of refraction of a light beam, passing through the gas when charged particles pass through it.

A further object of the invention is to provide an optical detector of ionizing radiation which uses optical interferometry to detect charged particles via a change in the index of refraction of an ionized gas when a light beam passes through it.

A further object of the invention is to provide an optical ionization detector which utilizes a gas filled region subjected to a high electric field for detecting charged particles via the change in density of the gas.

Another object of the invention is to provide an optical ionization detector which splits a beam of electromagnetic radiation into two arms, processes one arm of the beam in a gas-filled region subjected to a high electric field, passes the other arm of the beam through a fiber optic, and recombines the two arms of the beam.

Another object of the invention is to provide an optical ionization detector which utilizes a change in the index of refraction for indication of a charged particle passing through the detector.

Other objects and advantages of the invention will become apparent from the following description and accompanying drawings.

Basically, the present invention is directed to a detector of ionizing radiation which uses optical interferometry to detect density changes in a gas when charged particles pass through the gas. More specifically, the optical ionization detector includes a gas-filled region subjected to a high electric field and as a charged particle traverses the gas region an electron is freed and accelerated to form an avalanche of electrons which effects the density of the gas, and since the index of refraction is proportional to the gas density, the index of refraction will change, and this index change is used by splitting a beam of light radiation after the index of refraction in one arm has been changed, and recombining the beam arms, whereby the index change leads to interference between the two beam arms, and when recombined give rise to measurable interference fringe changes that are a function of the index change, and so indicate the passage of a charged particle through the gaseous medium.

The present invention provides a detector particularly adapted for detecting muons generated in the collisions of high energy proton-proton, or electron-positron pairs, but is also sensitive to other types of radiation such as gamma rays, electrons and proton. In addition, the optical nature of the signals produced by this detector make optical trigger processing possible, leading to reduced cabling volume and noise problems. Thus, the invention may be utilized in a number of different high energy and nuclear physics applications.

BRIEF DESCRIPTION OF THE DRAWINGS

The accompanying drawings, which are incorporated into and form a part of the disclosure, illustrate the embodiments of the invention and, together with the description, serve to explain the principles of the invention.

FIG. 1 is a schematic view of an embodiment of the optical ionization chamber in accordance with the invention.

FIG. 2 is a schematic representation of a parallel plate (microgap) type gas-filled counter for utilization in the FIG. 1 embodiment.

FIG. 3 is a schematic representation of a concentric electrode (cylindrical) types gas-filled counter for utilization in the FIG. 1 embodiment.

DETAILED DESCRIPTION OF THE INVENTION

The optical ionization detector of the present invention basically comprises a detector of ionizing radiation which uses optical interferometry to detect density changes in a gas when charged particles pass through it. The detector involves splitting a beam of electromagnetic radiation, such as a produced via a laser diode, into two arms, with one arm expanded and traveling through a gas-filled region and the other arm traveling through a single-mode optical fiber, and recombining the two arms, to indicate, via optical interferometry as described hereinafter, the passage of a charged particle through the gaseous medium. The gas filled region is subjected to a high electric field, and as charged particle traverses this gas region, electrons are freed from the gas atoms when the gas is ionized by the particle. These liberated electrons are accelerated toward an anode and as they accelerate, more electrons are liberated, thus forming an avalanche of electrons. The number of electrons in the avalanche is a function of the accelerating voltage, the gas, and the gas pressure. Typically, for a gas mixture of 90% argon, 10% methane (known as P10), a voltage of about 500 volts, and a gas pressure of ~1 atm. for a microgap parallel plate type counter with a part separation of about 100 microns, or for a cylindrical counter with a one centimeter radius and a 50 micron diameter anode wire at about 1000 volts, with the same gas and gas pressure as in the parallel plate counter, the "gas gain" is about $10^6$, i.e., about $10^6$ electrons and ions are formed. The electrons drift with a characteristic velocity toward the anode and the ions drift with a different velocity toward the cathode. Typically, in argon, drift velocities are about $8 \times 10^6$ cm/s for electrons and $5 \times 10^5$ cm/s for ions. For the 100 micron planar ionization chamber or counter, this corresponds to an electron drift time of 1.3 ns and an ion drift time of about 20 ns. For the one centimeter diameter cylindrical ionization chamber or counter, this corresponds to an electron drift time of 31.3 ns and an ion drift time of 500 ns. The average velocity (v) of argon gas atoms at room temperature is given by the expression $v = (3 KT/m)^{\frac{1}{2}}$, where K is the Boltzmann constant, T is the temperature, and m is the mass of an argon atom. This gives $v = 1.35 \times 10^3$ cm/s, and thus for a 100 micron ($10^{-2}$ cm) distance of the planar chamber, the gas will be depleted for a time equal to $7.40 \times 10^{-4}$ s/cm $\times 10^{-2}$ cm $= 7.40 \times 10^{-6}$ s. Thus, with the planar ionization chamber, the depletion time is seen to be, on average, about 100 to 1000 times longer than the avalanche formation and drift time. For the 0.25 cm average distance of the cylindrical chamber, the gas will be depleted for a time equal to $1.85 \times 10^{-4}$ s, and the depletion time would be about 300 to 6000 times longer than the avalanche formation and drift time.

The gas density is therefore affected by the formation of the electron avalanche by about one part in $10^6$, $1:10^6$, if the "gas gain" is $10^6$. Assuming that the index of refraction is proportional to the gas density, then the index of refraction will also change by one part in $10^6$, $1:10^6$.

The optical ionization detector of this invention uses this index of refraction change by modulating the one arm of the split laser beam passing through the gas, with respect to the other arm of the laser beam passing through a fiber optic. Small index changes can lead to interference between the arms of the beam, which, when combined, give rise to measurable interference fringe changes that are a function of the index change, and so indicate the passage of a charged particle through the gaseous medium of the detector.

Referring now to the drawings, FIG. 1 schematically illustrates the optical ionization detector is which a beam of electromagnetic radiation, such as laser light beam 10, is emitted from a source, such as laser diode 11, and split by a conventional beam splitter 12 to form two arms or beams 13 and 14. Beam arm 13 is directed into an ionization chamber generally indicated at 15 via an optical lens 16 which expands the beam as indicated at 13' and exits from chamber 15 via an optical lens 17 which reduces beam 13' as indicated at 13", and passes into beam interference detection electronics generally indicated at 18. Beam arm 14 from splitter 12, which constitutes a reference beam, passes through a single-mode optical fiber 19 and is recombined with beam arm 13" in interference detection electrons 18. For example, the arm 13 is expanded by lens 16 from a 100 μm diameter cross-section to a 1 cm diameter cross-section, and then reduced by lens 12 to the original cross-section. The beam is expanded to interrogate as much of the gas region as possible.

Within the ionization chamber 15, which contains a gas 20 and across which is applied an electrical potential, as described above, an electron avalanche indicated at 21 is generated when a charged particle indicated at 22 traverse this gas region, as described above and hereafter with respect to FIGS. 2 and 3. The gas 29 may be an argon/methane mixture, argon/isobutane or $CO_2/CF_4$, at a pressure of 0.1 atm. to 2 atm. FIG. 2 illustrates a microgap parallel plate type counter or ionization chamber, while FIG. 3 illustrates a cylindrical type counter or ionization chamber, and either of the FIG. 2 or FIG. 3 chambers may be utilized in the detector of FIG. 1, and thus each is given the reference number 15.

The FIG. 2 chamber 15, as broadly described above, includes a pair of parallel plates which constitute at cathode 23 and an anode 24 separated by a gas-filled gap or region 25 through which light beam 13' passes. A voltage is applied between the anode and cathode from a power supply as indicated by conventional symbols to produce a high electric field through the gap 25, as described above. Thus, as a charged particle 22 strikes the cathode 23 or traverses the gas 20, electrons are freed or liberated and are thereafter accelerated to form electron avalanches 21 which are collected by anode 24, as described above. The density of gas 20 is affected by the formation of the electron avalanche and thus, as described above, causes a change in the index of refraction of the light beam 13' which is reduced via optic lens 17 at beam 13". As pointed out above, small index changes can lead to interference between that modulated light beam arm 13" and the reference light beam arm 14, which, when recombined, give rise to measurable interference fringe changes that are a function of the index change, and so indicate the passage of a charged particle through the gaseous medium within the ionization chamber. The technique for obtaining the interference fringe changes produced from recombining the modulated light beam arm 13″ and the reference light beam arm 14 are known in the art. Thus, further description or illustration of the apparatus indicated generally at 18 for determining the interference fringe changes is deemed unnecessary.

The FIG. 3 ionization chamber 15 constitutes a conventional gas-filled cathode tube and basically comprises a pair of concentric spaced electrodes with the outer electrode constituting a cathode 26 and the inner electrode constituting an anode 27 with the space there between filled with a gas 20. While not shown, a power supply is connected to apply a voltage between anode 27 and cathode 26 to produce an electric field there between, as above described. Thus, when a charged particle 22 strikes the cathode 26 electrons are liberated and accelerated to form electron avalanches 21, as described above, which affects the density of gas 20 and thus the index of refraction of light beam 13′, whereby the passage of a charged particle through the gaseous medium 20 can be detected, as described above.

The above-described optical ionization detector of this invention can be used to detect ionizations from natural and man-made sources, such as radioactive isotopes, and underground nuclear tests. Large arrays of detector elements can be assembled into a hodoscope, for example, to measure radiation patterns emanating from nuclear fusion by-products. Individual detectors could be used as area monitors for personnel radiation monitoring. The optical nature of the signal is especially desirable for long cable runs, such as those in underground nuclear testing and they have the added advantage of being less susceptible to noise pickup. As pointed out above, the detector is sensitive to various types of ionizing radiation including gamma rays, electrons, protons, and muons and can find use in a number of high energy and nuclear physics applications.

While a particular embodiment of the optical ionization detector of the invention and embodiments of ionization chambers, as well as specific materials and parameters for the detector have been described and illustrated, such is not intended to limit the invention to that described and/or illustrated. Modifications and changes will become apparent to those skilled in the art and it is intended that all such modification and changes fall within the scope of the invention, and only the appended claims limit the scope of the invention.

We claim:

1. An optical ionization detector of ionizing radiation using optical interferometry, comprising:
   means for splitting a beam of light into two arms;
   an ionization chamber;
   said ionization chamber having therein a cathode and an anode in spaced relation to form a gap there between;
   an ionizable gas contained in said chamber;
   means for producing an electric field within said gap;
   a fiber optic with one end thereof positioned adjacent said beam splitting means;
   means for combining said two arms of said beam of light after one of said arms has passed through said ionization chamber;
   whereby one of the arms of a beam of light in passage through said ionization chamber and the other of the arms of the beam of light is passed through said fiber optic, such that upon a charged particle striking said ionization chamber an electron avalanche is generated causing a change in the index of refraction of the light beam arm passing through the ionization chamber, and where after the two arms of the light beam are recombined and the change of the index of refraction of the one light beam arm results in measurable interference fringe changes indicating the passage of a charged particle through the ionization chamber.

2. The detector of claim 1, additionally including means for expanding the one arm of the light beam as it passes into said ionization chamber, and means for reducing the expanded arm of the light beam to an original size as it passes out of said chamber.

3. The detector of claim 1, wherein said cathode and said anode are of a planar configuration defining said gap there between.

4. The detector of claim 3, wherein said gap has a width of about 100 microns, and wherein said means for producing an electric field within said gap includes a power supply connected to said anode and said cathode and capable of producing about 500 volts.

5. The detector of claim 1, wherein said cathode and said anode are of a concentric configuration defining said gap there between.

6. The detector of claim 5, wherein said anode has a diameter of about 50 microns and wherein said gap has a diameter of about one centimeter.

7. The detector of claim 1, wherein said gas is selected from the group of an argon/methane mixture, argon/isobutane, and $CO_2/CF_4$, with a pressure in the range of 0.1 atm. to 2 atm.

8. The detector of claim 1, wherein said gas is a 90% argon, 10% methane mixture at a pressure of 1 atm.

9. The detector of claim 1, additionally including means for producing a beam of light directed onto said means for splitting the light beam.

10. A method for detecting the passage of a charged particle through a beam of light by a change of index of refraction in the light beam, including the steps of:
    splitting a beam of light into two arms;
    directing one arm of the light beam into an ionization chamber;
    directing the other arm of the light beam through a fiber optic;
    providing the ionization chamber with an ionizable gas;
    forming an electric field through the gas such that upon a charged particle being directed into the gas causes at least one electron to be freed when the gas is ionized by the charged particle and accelerated through by electric field causing the generation of an electron avalanche;
    passing the one arm of the light beam through the gas whereby an electron avalanche causes a change in the density of the gas and a corresponding change in the index of refraction of the gas within the light beam arm passing therethrough;
    directing the one arm of the light beam out of the ionization chamber;
    recombining the two arms of the light beam; and
    determining the passage of a charged particle through the gas in the ionization chamber via the measurable interference fringe changes in the two arms of the light beam due to the change of the index of refraction of the one light beam arm.

11. The method of claim 10, additionally including the steps of expanding the one arm of the light beam as it passes into the ionization chamber, and reducing the one arm of the light beam to its original size as it passes out of the ionization chamber.

12. The method of claim 10, additionally including the step of forming the ionization chamber by: positioning a cathode and an anode in spaced relation to form a gap there between, and applying an electric potential between the anode and the cathode for producing the electric field through the ionizable gas in the thus formed gap.

13. The method of claim 12, additionally including the steps of forming the cathode and the anode in a planar configuration, and positioning the cathode and anode such that the gap there between has a width of about 100 microns.

14. The method of claim 13, wherein the step of applying an electric potential between the anode and the cathode for producing the electric field is carried out by connecting a power supply of about 500 volts between the anode and the cathode.

15. The method of claim 12, additionally including the step of forming the cathode and the anode in a concentric configuration, and positioning the cathode and anode such that the gap there between has a diameter of about one centimeter.

16. The method of claim 10, wherein the step of providing the ionization chamber with an ionizable gas is carried out by providing an ionizable gas selected from the group consisting of an argon/methane mixture, argon/isobutane, and $CO_2/CF_4$, at a pressure of 0.1 atm. to 2 atm.

17. The method of claim 16, wherein the step of providing the ionizable gas is carried out by selecting a 90% argon, 10% methane mixture at a pressure of 1 atm.

18. A detector of ionizing radiation using optical interferometry to detect density changes in a gas when charged particles pass through the gas, comprising:
   means for producing a beam of light;
   means for splitting said light beam into a plurality of arms;
   fiber optic means having one end adjacent said light beam splitting means for receiving one of said arms of said light beam;
   an ionization chamber positioned to receive another of said arms of said light beam;
   said ionization chamber including an ionizable gas and means for producing an electric field through at least a portion of said gas, such that when a charged particle traverses the gas it frees an electron which is accelerated in said electric field to form an electron avalanche which changes the density of the gas which causes a change in the index of refraction of the gas as a light beam passes therethrough;
   said other arm of said light beam passing through said ionizable gas in said ionization chamber exiting from said chamber, and passing to a point of recombining with said one arm of said light beam as it exits from said fiber optic means; and
   means for measuring interference changes that are a function of the index of refraction change in said other arm of said light beam, thereby providing an indication of the passage of a charged particle through the ionizable gas.

19. The detector of claim 18, additionally including means for expanding said other arm of said light beam as it enters said ionization chamber, and means for reducing said expanded arm of said light beam as it exits from said ionization chamber.

20. The detector of claim 18, wherein said means for producing an electric field through said gas includes a cathode, an anode, said cathode and anode being positioned so as to define a gap there between, and means connected to said cathode and anode for producing an electric potential there between which forms said electric field.

* * * * *